United States Patent [19]

Patt et al.

[11] 4,430,495

[45] Feb. 7, 1984

[54] PROCESS FOR PREPARING LINCOMYCIN AND CLINDAMYCIN RIBONUCLEOTIDES

[75] Inventors: Tom E. Patt, Kalamazoo; Alexander D. Argoudelis, Portage; Vincent P. Marshall, Kalamazoo, all of Mich.

[73] Assignee: The Upjohn Company, Kalamazoo, Mich.

[21] Appl. No.: 419,244

[22] Filed: Sep. 17, 1982

[51] Int. Cl.$^3$ .............................................. C07H 15/16
[52] U.S. Cl. .................................. 536/16.3; 536/16.2; 536/16.4; 536/16.5; 536/28; 536/29
[58] Field of Search ..................... 536/16.2, 16.3, 16.4, 536/16.5

[56] References Cited

U.S. PATENT DOCUMENTS

| | | | |
|---|---|---|---|
| 3,671,647 | 6/1972 | Argoudelis et al. | 536/16.3 |
| 4,278,789 | 7/1981 | Birkenmeyer | 536/16.3 |
| 4,310,660 | 1/1982 | Birkenmeyer | 536/16.3 |
| 4,383,109 | 5/1983 | Argoudelis et al. | 536/16.2 |

Primary Examiner—Johnnie R. Brown
Attorney, Agent, or Firm—Roman Saliwanchik

[57] ABSTRACT

Novel and useful ribonucleotides of analogs of the well known antibiotics lincomycin and clindamycin. These ribonucleotides are unexpectedly highly active against Streptococcus hemolyticus and Staphylococcus aureus in vivo. These ribonucleotides are prepared by using resting cell or cell-free extracts of Streptomyces rochei, NRRL 3533, or cell-free extracts of Streptomyces coelicolor, NRRL 3532.

5 Claims, No Drawings

PROCESS FOR PREPARING LINCOMYCIN AND CLINDAMYCIN RIBONUCLEOTIDES

DESCRIPTION

BACKGROUND OF THE INVENTION

The characteristics and preparation of the antibiotic lincomycin are disclosed in U.S. Pat. No. 3,086,912. Clindamycin is disclosed in U.S. Pat. No. 3,496,163. These antibiotics have been extensively used as medicines in humans and animals. A number of patents world-wide have issued concerning these antibiotics and a variety of derivatives thereof.

The structural formulas for lincomycin (1) and clindamycin (2) are shown in Chart 1.

Lincomycin and clindamycin 3-nucleotides are disclosed and claimed in U.S. Pat. No. 3,671,647. All of the lincomycin and clindamycin compounds disclosed in U.S. Pat. No. 3,671,647 have the propyl hygric acid moiety. These 3-nucleotides were found by test against *S. aureus* in vivo to have an activity approximately one-tenth of the parent compound.

U.S. application Ser. No. 255,542 now U.S. Pat. No. 4,383,109, discloses the preparation of 3-ribonucleotides of lincomycin- and clindamycin-type compounds by cultivating the well-known and publicly available microbe *Streptomyces rochei*, NRRL 3533, in an aqueous, aerated, fermentation.

BRIEF SUMMARY OF THE INVENTION

The subject invention concerns the preparation of 3-ribonucleotides of lincomycin- and clindamycin-type compounds by cell-free extracts of *Streptomyces coelicolor* and resting cells or cell-free extracts of *Streptomyces rochei*. The novel 3-ribonucleotides of the subject invention cannot be prepared by whole cell systems of the above organisms. Thus, there is a patentable distinction between the compounds and processes of this application and the disclosure in the art, discussed above.

Unexpectedly, the nucleotides of the subject application demonstrate in vivo antibacterial activity as high as the parent compounds. Because of these highly relevant characteristics, the nucleotides of the subject invention are considered to be prime candidates for medicinal use.

The lincomycin- and clindamycin-type compounds which can be converted to the 3-ribonucleotides are shown in Chart 2. In place of the hydroxyl at the three position of the lincosaminide moiety, there is substituted a nucleotide selected from the group shown in Chart 3. Specifically exemplified in the subject disclosure is the preparation of pirlimycin 3-(5'-inosinate) which is shown in Chart 4. It should be recognized that the other ribonucleotides disclosed in Chart 3 can be used to make the 3-ribonucleotides of the other lincomycin- and clindamycin-type compounds shown in Chart 2 by the process disclosed herein. With reference to Chart 3, the purines within the scope of the invention are described in Tables 21 to 58 of the publication entitled "FUSED PYRIMIDINES" PART II. Purines. Edited by D. T. Brown, Wiley-Interscience, New York. This publication is the twenty-fourth volume in the series "THE CHEMISTRY OF HETEROCYCLIC COMPOUND." Examples of purines within the scope of the subject invention are as follows: 1,3,7-Trimethylxanthine; 2-Amino-1,6-dihydropurine; 1,2,3,6-Tetrahydro-2-oxopurine; 7-Methylguanine; 7-Methylxanthine; 1,6-Dihydro-6-oxopurine; 2-Aminopurine; 1,3,-Dimethylxanthine; 6-Amino-2,3-dihydro-2-oxopurine; 2-Furfurylaminopurine; 4(5)-Substituted uric acid; 6-Furfurylaminopurine; 6-Mercaptopurine; 1,6-Dihydro-6-thiopurine; 1,7-Dimethylxanthine; Hypoxanthine; 1-Methyladenine; 3,7-Dimethylxanthine; 1,3-Dimethylxanthine; 2-Amino-1,6-dihydro-6-thiopurine; 6-Amino-3-(3-methylbut-2-enyl)purine; and 6-(4-Hydroxy-3-methylbut-2-enyl)aminopurine.

The pyrimidines within the scope of the invention include both simple and substituted pyrimidines as described in the publication entitled "THE PYRIMIDINES" Supplement I, Edited by D. T. Brown, Wiley-Interscience, New York. This publication is the sixteenth volume in the series "THE CHEMISTRY OF HETEROCYCLIC COMPOUND." Examples of pyrimidines within the scope of the subject invention are as follows: 2-Amino-4,6-dihydroxypyrimidine; 4,5-(and 4,6)Diamino-2-hydroxypyrimidine; 5-(and 6-)Amino-2,4-dihydroxypyrimidine; 2,4,6-Trihydroxypyrimidine; 5-Bromo-2,4-dihydroxypyrimidine; Tetrahydroxypyrimidine; 4,5,6-Triamino-2-hydroxypyrimidine; 4,5-Diamino-2,6-dihydroxypyrimidine; 2,4,6-Trihydroxy-5-nitropyrimidine; 2,4-Dimercaptopyrimidine; 2,4-Diamino-5,6-dihydroxypyrimidine; 4,5-Dihydro-2,6-dihydroxypyrimidine; 2,4,5-Trihydroxypyrimidine; 2-Amino-4-hydroxypyrimidine; 4,5-Dihydro-2,4,6-trihydroxy-5-oxopyrimidine; 2,5-Dihydroxypyrimidine; 4-Amino-2,5,6-trihydroxypyrimidine; 2,4,5-Trihydroxy-6-nitrosopyrimidine; Hexahydrotetraoxopyrimidine; 4-Amino-2-hydroxy-5-methylpyrimidine; 2,4-Dihydroxy-5-nitropyrimidine; 4-Carboxy-2,6-dihydroxypyrimidine; 2,4,6-Trihydroxy-5-ureidopyrimidine; Tetrahydroxypyrimidine; 4,6-Dihydroxy-2-mercaptopyrimidine; 5-Amino-4,6-dihydroxy-2-mercaptopyrimidine; 4-(and 2-)Hydroxy-2-(and 4-)mercaptopyrimidine; 2,4-Dihydroxy-5-methylpyrimidine; 2,4-Dihydroxy-5-hydroxymethylpyrimidine; 5-Amino-2,4,6-trihydroxypyrimidine; and 2,4,6-Trihydroxy-5-nitrosopyrimidine.

The purine and pyrimidine nucleoside triphosphates needed for the enzymatic nucleotidylation of lincosaminides can be prepared by several methods already reported in the literature. (A. M. Michelson "The Chemistry of Nucleosides and Nucleotides, Academic Press, New York, 1963).

DETAILED DESCRIPTION

The parent compounds disclosed in Chart 2 can be prepared by the procedures disclosed in U.S. Pat. No. 4,278,789.

The 3-(5'-ribonucleotides) of the compounds of Chart 2 can be prepared by following the procedures disclosed in U.S. Pat. No. 3,671,647. Salts of these nucleotides also can be prepared following the procedures in U.S. Pat. No. 3,671,647.

Formulations of the nucleotides of this invention can be made following the composition examples in U.S. Pat. No. 4,278,789. The formulations are prepared by substituting a nucleotide of the subject invention for the active compound in the examples. The substitution can be on an equimolar basis.

General assay and characterization procedures which can be employed to determine and characterize the nucleotides of the invention are as follows:

Assay of 3-(5'-Ribonucleotides)

Since the 3-ribonucleotides of this invention lack in vitro antibacterial activity, their formation from the antibacterially-active parent compounds can be followed easily by measuring the loss of such antibiotic activity. To determine the amounts of antibacterially-active parent compound in culture filtrates or reaction mixtures, a standard assay with *Sarcina lutea* ATCC 9341 is employed. To assay for the presence of the 3-ribonucleotides in fermentation beers, extracts, and purified materials, the phosphodiester bond is first hydrolyzed with crude alkaline phosphatase, or snake venom phosphodiesterase, by the procedures described below. The antibacterially-active compound in the hydrolysate is determined by standard assay.

Enzymatic Hydrolyses

Alkaline Phosphatase: Stock solutions (0.5 mg/ml, 0.54 Units/mg) of pigeon intestine alkaline phosphatase, EC 3.1.3.1 (Sigma) are prepared in Tris (hydroxymethyl) aminomethane hydrochloride buffer, 0.01 M pH 8.0. Samples to be treated are diluted 1:2 with the enzyme buffer mixture and are incubated at 28° C. for 18 hours.

Snake Venom Phosphodiesterase: Stock solutions (100 mg/ml, 0.026 Units/mg) of purified snake venom phosphodiesterase EC 3.1.4.1 (Sigma) are prepared in distilled water. Incubation mixtures contain 0.2 ml of a solution (1 mg/ml) of the sample to be treated in water, 0.6 ml of 0.01 M Tris-hydrochloride buffer, pH 9.0, 0.1 ml of 0.3 M $MgCl_2$, and 0.1 ml of the enzyme stock solution. Incubation is carried out at 37° C. for 18 hours.

Spleen Phosphodiesterase: Stock solutions of spleen phosphodiesterase EC 3.1.4.18 (Sigma) are prepared (1 mg/ml, 19.6 Units/mg) in distilled water. Incubation mixtures contain 0.4 ml of a solution (0.5 mg/ml) of the sample to be treated in water, 0.5 ml of 0.02 M Tris buffer, pH 7.0 and 0.1 ml of the enzyme stock solution. Incubation is carried out at 37° C. for 18 hours.

Thin-Layer Chromatographic Analysis of Preparations and Enzymatic Hydrolysates

The production and purification of the 3-ribonucleotides is followed by assay against *S. lutea* (see above) and by TLC using silica gel G and methyl ether ketone-acetone-water (186:52:20, v/v) or ethyl acetate-acetone-water (8:5:1) as the solvent systems. The bioactive parent compounds are detected by bioautography on agar seeded with *S. lutea*.

The products of enzymatic or chemical hydrolysis of the 3-nucleotides are separated by the following TLC systems:

A: Silica gel GF plates (Analtech Inc.); water as the solvent system.
B: Silica gel GF plates; n-propyl alcohol-conc. ammonium hydroxide-water (55:10:35, v/v).
C: NM-Polygram Cellulose 300 (Brinkman Instruments Inc.); 1-butanol-water-formic acid (77:13:10, v/v).

UV absorbing materials are detected by a short wavelength UV lamp. Bioinactive, UV-nonabsorbing materials are detected by a permanganate-periodate spray reagent. Bioactive nucleotide materials are detected by bioautography on agar seeded with *S. lutea*.

The following example shows the preparation of the nucleotide of the compound designated as U-57930E and named pirlimycin. The structural formula of U-57930E is shown in Chart 4. By following the procedures of this example, or obvious equivalents thereof, there can be made the 3-ribonucleotides of the other compounds disclosed in Chart 2.

The following example is illustrative of the process and products of the invention, but are not to be construed as limiting. All percentages are by weight and all solvent mixture proportions are by volume unless otherwise noted.

EXAMPLE 1

Cell-Free Extracts of *Streptomyces coelicolor*

A. Growth of *S. coelicolor*, NRRL 3532.

*S. coelicolor* is stored and maintained on sterile soils. The *S. coelicolor* containing soils are inoculated into a seed medium termed GS-7 which contains Pharmamedia (Traders Oil Mill Co.) and Cerelose (C.P.C. International) each added at 25 g per 1 of tap $H_2O$. The pH of GS-7 are shaken at 250 rpm in wide-mouth 500 ml fermentation flasks for 72 hours at 28° C. The mature seed cultures are used as a source of inoculum (5% V/V) for a production medium which contains glucose (Mallinckrodt), 20 g; yeast extract (Difco), 2.5 g; NZ-amine type B (Sheffield Co.), 5 g; $NaNO_3$, 1.5 g and $FeSO_4$, 10 mg added per liter of deonized $H_2O$. After formation, the pH adjustment and sterilization of this medium is performed as with GS-7. *S. coelicolor* is subsequently grown for 24 hours in the production medium in the manner described for the seed culture.

B. Harvest of *S. coelicolor*

Twenty-four hr cultures of *S. coelicolor* are harvested by centrifugation at 5000 xg for 15 min. The pellet obtained in this procedure is resuspended into 100 mM potassium phosphate, pH 7 and the centrifugation procedure is repeated. All operations are performed in the cold and the washed *S. coelicolor* pellets are maintained in a frozen state.

C. Preparation of the *S. coelicolor* cell-free extract

Frozen *S. coelicolor* paste is thawed and resuspended into 10 mM potassium phosphate, pH 7.5 containing EDTA at 0.5 mg per ml. The resuspended *S. coelicolor* mycelia is exposed to lysozyme (Sigma) at 1 mg per ml and is mixed at room temperature for 1 hr. The mixture is subsequently centrifuged for 15 min at $10^4$ xg at 0° C. The supernatant fluid is retained as the cell-free extract.

EXAMPLE 2

Preparation of Pirlimycin 3-(5′-Inosinate)

The reaction mixture contains *S. coelicolor* cell-free extract protein, prepared as described in Example 1, 200 ml of a 12 mg/ml solution or 2.6 g; inosine triphosphate, 400 ml of 0.1 M solution in pH 7.0 phosphate buffer or 40 mmoles of ITP (Sigma); magnesium chloride, 200 ml of 0.2 M solution or 40 mmoles; potassium phosphate, 200 ml of 0.1 M solution in water or 20 mmoles; pirlimycin, 300 ml of a 2 mg/ml solution in water or 600 mg; water 700 ml. The pH of the completed reaction mixture is adjusted to 6.5 and the mixture is incubated at 28° C.

A total of 2.0 g of pirlimycin is transformed to pirlimycin 3-(5′-inosinate) by this procedure.

Assay of Pirlimycin concentration

The concentration of pirlimycin is determined experimentally by its bioactivity vs. micrococcus luteus, ATCC 9341. One biounit of anti-*M. luteus* activity is found to be equivalent to ca. 1 μg of pirlimycin. One biounit is the amount of antibacterial activity required to produce a zone of *M. luteus* growth inhibition of 20 mm when 0.08 ml of reaction mixture is placed on a 12 mm paper disc (Schleicher and Schuell, No. 740-E).

EXAMPLE 3

Adenylation of Pirlimycin by *Streptomyces coelicolor* Cell-Free Extract

The following is an example pertaining to the adenylation of 2 g of pirlimycin using the procedure described above. The 2 l reaction mixture employed in this conversion contains *S. coelicolor* cell-free extract (protein), 200 mg; ATP, 40 mmoles; $MgCl_2$, 40 mmoles; potassium phosphate, 20 mmoles and pirlimycin 2 g. The complete reaction mixture is subsequently incubated with mixing for 24 hrs at 28° C. following adjustment of the pH to 6.5 to give pirlimycin 3-(5'-adenylate).

EXAMPLE 4

Upon following the procedures of Examples 1–3, but substituting the other ribonucleotides depicted in Chart 3 for the ribonucleotides in Examples 2 and 3, there are obtained the corresponding pirlimycin 3-(5'-ribonucleotides).

EXAMPLE 5

Upon following the procedures of Examples 1–3, but substituting the other lincomycin- and clindamycin-type compounds depicted in Chart 2 for pirlimycin in Examples 2 and 3 there are obtained the corresponding lincomycin- and clindamycin-type compound 3-(5'-ribonucleotides).

EXAMPLE 6

Upon following the procedures of Examples 1–3, but substituting other lincomycin- and clindamycin-type compounds depicted in Chart 2 for pirlimycin in Examples 2 and 3, and other ribonucleotides depicted in Chart 3 for the ribonucleotides in Examples 2 and 3, there are obtained the corresponding lincomycin- and clindamycin-type 3-(5'-ribonucleotides).

EXAMPLE 7

Isolation of Pirlimycin 3-(5'-Inosinate) Prepared in Example 2

A reaction mixture containing 600 mg of pirlimycin 3 (5'-inosinate) as the substrate is adjusted to pH 6.5 and chromatographed over 300 ml of Amberlite XAD-2. The spent is discarded. The column is washed with 1 L of water. The water wash is also discarded. The column is then eluted with methanol-water (70:30 V/V). Six fractions are collected and designated methanol-1 (100 ml), methanol-2 (200 ml), methanol-3 (200 ml), methanol-4 (500 ml), methanol-5 (500 ml) and methanol-6 (500 ml).

Fractions methanol-2 to methanol-6 containing pirlimycin 3-(5'-inosinate) are combined and the resulting solution is concentrated to an aqueous and freeze-dried to give preparation ADA-18.1, 900 mg of pirlimycin 3-(5'-inosinate).

EXAMPLE 8

Purification of Pirlimycin 3-(5'-(Inosinate)

DEAE-Sephadex (Acetate) Chromatograph

The column is prepared from 300 g of DEAE-Sephedex transformed in the acetate form. The resin was packed and equilibrated with 0.03 M tris(hydroxymethyl)aminomethane (THAM) acetate pH 8.0 buffer.

Starting material, 3030 mg, (obtained from enzymatic transformation of 2.0 g of pirlimycin) are combined and dissolved in 50 ml of THAM acetate, pH 8.0 buffer and added on the top of the column. The column is eluted with:

1. 0.03 M THAM acetate pH 8.0; fractions 1-1156.
2. 0.06 M THAM acetate pH 8.0; fractions 1157-1750.

Fractions of 20 ml are analyzed by testing for bioactivity before and after treatment with alkaline phosphatase and by U.V. measurement.

Fractions 670–1650 are found to contain pirlimycin inosinate; they are combined and this solution was treated as described below:

Removal of THAM Acetate Buffer. Amberlite XAD-2 Chromatography

The column is prepared from 300 ml of Amberlite XAD-2. Starting material, the pool obtained by DEAE-Sephadex chromatography (see above) is adjusted to pH 6.5 and passed over the column at a rate of 10 ml per minute. The spent solution is found free of pirlimycin inosinate and is discarded. The column is washed with 1100 ml of water. The aqueous wash is discarded. The column is then eluted with methanol water (70:30 V/V). Fractions methanol-1 (500 ml) and methanol-2 (500 ml), containing pirlimycin inosinate are combined, concentrated to an aqueous solution and freeze-dried to give 540 mg, of essentially pure pirlimycin inosinate.

Pirlimycin 3-(5'-inosinate) has a molecular weight of 740. The UV spectrum is identical to that reported for inosine phosphate. Upon treatment with alkaline phosphatase there is obtained pirlimycin and inosine. Treatment with phosphodiesterase T (snake venom phosphodiesterase, phosphodiesterase I, catalyzes the hydrolysis of oligonucleotides, i.e., ribo- or deoxyribo, with free 3'-hydroxyl end group to yield mononucleoside 5'-phosphates) yields pirlimycin and inosine 5'-phosphate. Treatment with phosphodiesterase II (spleen phosphodiesterase II acts as an exonuclease and yields nucleoside-3'-phosphates) fails to degrade the pirlimycin 3-(5'-inosinate) obtained.

Mass spectroscopic analysis using fast atom bombardment (FAB) of the pirlimycin 3-(5'-inosinate) obtained follows:

| | FAB MS of Pirlimycin 3-(5'-Inosinate) |
|---|---|
| Data Rate: 2500 HZ. | Seq. No.: 9 |
| Max. Raw Int.: 788 | Tot. Ion.: 1 |
| Scale Factor: 10 | Accel. Voltage: 3.0 KV |
| El. Energy: 70.0 EV | Inj. System: Probe-EI |
| Probe Temp: 5.6° C. | Source Temp: 260.0° C. |
| Mol. Weight: 740 | Mol. Formula $C_{27}H_{42}CL_1N_6O_{12}P_1S_1$ |
| Ex. Mol. Weight: 740.2007 | Name: Pirlimycin Inosinate |
| Average of 8 Scans | |

Most Intense Ions:

| 112 (9999) | 56 (3421) | 113 (1788) | 741 (1763) | 137 (1209) |
|---|---|---|---|---|
| 110 (1162) | 55 (1131) | 97 (939) | 743 (924) | 82 (789) |

| M/Z | | | | | | INTENSITY | | | | | | | |
|---|---|---|---|---|---|---|---|---|---|---|---|---|---|
| + | 0 | 1 | 2 | 3 | 4 | 5 | 6 | 7 | 8 | 9 | 10 | 11 | 12 | 13 |
| 15 | 33 | 0 | 3 | 74 | 50 | 0 | 0 | 0 | 17 | 0 | 0 | 7 | 171 | 261 |
| 29 | 291 | 673 | 146 | 4 | 0 | 0 | 6 | 0 | 0 | 5 | 314 | 27 | 681 | 436 |
| 43 | 535 | 340 | 230 | 65 | 42 | 4 | 22 | 1 | 22 | 22 | 183 | 269 | 1131 | 3421 |
| 57 | 501 | 155 | 51 | 60 | 356 | 15 | 40 | 3 | 81 | 39 | 282 | 274 | 607 | 507 |
| 71 | 162 | 230 | 117 | 37 | 124 | 12 | 106 | 36 | 124 | 207 | 432 | 789 | 533 | 686 |
| 85 | 195 | 222 | 125 | 35 | 88 | 52 | 153 | 263 | 205 | 237 | 225 | 272 | 939 | 362 |
| 99 | 233 | 71 | 43 | 28 | 99 | 28 | 42 | 63 | 74 | 182 | 146 | 1162 | 276 | 9999 |
| 113 | 1788 | 151 | 76 | 23 | 55 | 36 | 60 | 103 | 86 | 137 | 94 | 248 | 119 | 269 |
| 127 | 94 | 102 | 49 | 45 | 49 | 46 | 37 | 61 | 102 | 1209 | 264 | 211 | 213 |
| 141 | 70 | 151 | 66 | 47 | 43 | 70 | 45 | 49 | 54 | 86 | 101 | 125 | 86 | 121 |
| 155 | 135 | 62 | 226 | 87 | 36 | 43 | 35 | 47 | 55 | 64 | 53 | 57 | 77 | 44 |
| 169 | 48 | 54 | 41 | 38 | 28 | 32 | 31 | 43 | 44 | 46 | 130 | 71 | 51 | 64 |
| 183 | 62 | 43 | 38 | 30 | 28 | 54 | 32 | 53 | 36 | 59 | 45 | 41 | 60 | 51 |
| 197 | 308 | 70 | 34 | 29 | 31 | 48 | 32 | 20 | 98 | 39 | 217 | 64 | 26 |
| 211 | 78 | 39 | 42 | 22 | 55 | 40 | 40 | 33 | 37 | 28 | 25 | 21 | 24 | 43 |
| 225 | 37 | 30 | 28 | 20 | 51 | 15 | 98 | 29 | 66 | 35 | 29 | 35 | 19 | 21 |
| 239 | 20 | 16 | 20 | 23 | 20 | 14 | 23 | 25 | 16 | 19 | 28 | 14 | 28 | 30 |
| 253 | 52 | 38 | 24 | 17 | 26 | 14 | 27 | 30 | 244 | 47 | 93 | 25 | 19 | 15 |
| 267 | 15 | 16 | 11 | 11 | 23 | 53 | 28 | 37 | 180 | 39 | 64 | 30 | 13 | 14 |
| 281 | 16 | 10 | 14 | 12 | 15 | 14 | 17 | 11 | 41 | 17 | 80 | 22 | 35 | 14 |
| 295 | 13 | 11 | 12 | 11 | 18 | 9 | 28 | 13 | 30 | 26 | 22 | 21 | 11 | 7 |
| 309 | 27 | 12 | 14 | 5 | 14 | 7 | 16 | 16 | 26 | 13 | 16 | 8 | 29 | 14 |
| 323 | 22 | 22 | 12 | 9 | 26 | 11 | 54 | 19 | 28 | 13 | 19 | 17 | 14 | 12 |
| 337 | 13 | 7 | 11 | 11 | 8 | 5 | 26 | 11 | 144 | 37 | 68 | 22 | 66 | 20 |
| 351 | 49 | 28 | 14 | 13 | 11 | 7 | 15 | 13 | 17 | 7 | 26 | 15 | 116 | 35 |
| 365 | 54 | 15 | 13 | 7 | 3 | 1 | 7 | 5 | 14 | 6 | 39 | 14 | 33 | 10 |
| 379 | 15 | 8 | 11 | 6 | 9 | 4 | 8 | 2 | 17 | 17 | 11 | 18 | 29 | 14 |
| 393 | 75 | 24 | 49 | 13 | 23 | 6 | 5 | 4 | 11 | 2 | 9 | 2 | 12 | 3 |
| 407 | 15 | 7 | 51 | 18 | 690 | 163 | 269 | 65 | 30 | 5 | 7 | 5 | 10 | 5 |
| 421 | 9 | 3 | 27 | 3 | 30 | 7 | 24 | 11 | 9 | 6 | 5 | 1 | 8 | 7 |
| 435 | 11 | 4 | 15 | 5 | 17 | 5 | 35 | 11 | 170 | 35 | 69 | 14 | 10 | 2 |
| 449 | 6 | 2 | 6 | 1 | 9 | 4 | 30 | 6 | 45 | 12 | 27 | 11 | 11 | 0 |
| 463 | 4 | 2 | 5 | 8 | 5 | 6 | 8 | 5 | 27 | 10 | 258 | 58 | 120 | 26 |
| 477 | 25 | 3 | 5 | 1 | 11 | 4 | 12 | 6 | 18 | 6 | 17 | 5 | 34 | 7 |
| 491 | 512 | 124 | 212 | 49 | 27 | 5 | 5 | 2 | 11 | 3 | 7 | 3 | 17 | 1 |
| 505 | 18 | 5 | 9 | 1 | 6 | 1 | 4 | 1 | 6 | 1 | 12 | 3 | 13 | 3 |
| 519 | 8 | 3 | 5 | 1 | 7 | 1 | 3 | 1 | 4 | 1 | 16 | 1 | 10 | 2 |
| 533 | 42 | 8 | 24 | 4 | 7 | 1 | 30 | 7 | 13 | 4 | 5 | 0 | 8 | 2 |
| 547 | 7 | 1 | 6 | 0 | 17 | 4 | 24 | 7 | 10 | 3 | 23 | 5 | 125 | 3 |
| 561 | 9 | 0 | 14 | 2 | 11 | 3 | 8 | 4 | 19 | 5 | 24 | 9 | 11 | 2 |
| 575 | 6 | 1 | 6 | 3 | 3 | 0 | 5 | 0 | 1 | 0 | 7 | 1 | 60 | 24 |
| 589 | 33 | 13 | 11 | 1 | 5 | 1 | 3 | 1 | 2 | 1 | 2 | 1 | 3 | 10 |
| 603 | 20 | 17 | 111 | 33 | 47 | 13 | 6 | 1 | 3 | 0 | 1 | 1 | 0 | 1 |
| 617 | 1 | 0 | 3 | 1 | 10 | 2 | 4 | 1 | 0 | 0 | 2 | 0 | 1 | 2 |
| 631 | 6 | 3 | 4 | 3 | 3 | 1 | 2 | 0 | 1 | 0 | 1 | 0 | 1 | 1 |
| 645 | 3 | 1 | 1 | 1 | 1 | 1 | 1 | 0 | 0 | 0 | 1 | 7 | 2 | 5 |
| 659 | 3 | 1 | 1 | 2 | 0 | 0 | 3 | 0 | 1 | 0 | 1 | 1 | 1 | 0 |
| 673 | 3 | 0 | 3 | 1 | 4 | 3 | 4 | 1 | 1 | 0 | 0 | 0 | 1 | 0 |
| 687 | 2 | 1 | 2 | 1 | 10 | 2 | 13 | 5 | 25 | 6 | 13 | 5 | 1 | 1 |
| 701 | 1 | 1 | 1 | 0 | 35 | 13 | 22 | 14 | 10 | 1 | 2 | 4 | 7 | 5 |
| 715 | 4 | 3 | 6 | 3 | 3 | 0 | 7 | 1 | 24 | 9 | 36 | 17 | 38 | 14 |
| 729 | 15 | 6 | 4 | 1 | 1 | 0 | 2 | 0 | 1 | 3 | 85 | 36 | 1763 | 674 |
| 743 | 924 | 318 | 155 | 41 | 14 | 1 | 1 | 0 | 4 | 2 | 29 | 12 | 42 | 16 |
| 757 | 33 | 15 | 16 | 5 | 4 | 2 | 21 | 6 | 13 | 4 | 8 | 3 | 11 | 2 |
| 771 | 17 | 8 | 25 | 7 | 11 | 3 | 4 | 1 | 34 | 14 | 21 | 9 | 12 | 1 |
| 785 | 7 | 1 | 8 | 4 | 7 | 0 | 3 | 1 | 1 | 0 | 1 | 0 | 4 | 3 |
| 799 | 3 | 2 | 12 | 4 | 47 | 15 | 40 | 15 | 12 | 1 | 0 | 0 | 1 | 1 |
| 813 | 1 | 1 | 7 | 4 | 9 | 2 | 3 | 2 | 5 | 1 | 3 | 0 | 1 | 0 |
| 827 | 1 | 0 | 4 | 1 | 11 | 4 | 59 | 22 | 26 | 9 | 3 | 0 | 3 | 0 |
| 841 | 0 | 1 | 3 | 1 | 4 | 1 | 4 | 1 | 0 | 0 | 0 | 0 | 0 | 1 |

EXAMPLE 9

Isolation and Purification of Pirlimycin 3-(5'-Adenylate) from Cell-Free Reaction a. Amberlite XAD-2 Chromatography A 2-liter reaction mixture, described in Example 3, is passed over a column containing 400 ml of Amberlite XAD-2 at a rate of 25 ml/min. The column is then washed with 3 L of water. Both the spent and the water wash are tested for bioactivity before and after treatment with phosphatase. They are found bioinactive and are discarded. The column is then eluted with methanol-water (70:30) V/V). Fractions are analyzed by UV (at 260 nm). Active fractions are combined, concentrated to an aqueous solution and freeze-dried to give preparation ADA-6, 2.47 g. of pirlimycin 3-(5'-adenylate).

b. DEAE-Sephadex (Acetate) Chromatography

The column is prepared from 300 g of DEAE-Dephadex in the acetate form. The resin is equilibrated with 0.03 M tris-(hydroxymethyl) aminomethane (THAM) acetate pH 8.0 buffer. The starting material, preparation ADA-6, 2.47 g is dissolved in 50 ml of the buffer and added on the top of the column. The column is eluted with 0.03 THAM acetate pH 8.0 buffer. Fractions of 20 ml are collected and analyzed by U.V. spectroscopy (max at 260 nm). Results follow:

| Fraction No. | UV g max (OD) |
|---|---|
| 10 | no maximum |
| 20 | no maximum |
| 30 | no maximum |
| 40 | no maximum |
| : | : |
| : | : |
| 100 | no maximum |
| 110 | 260 (0.13) |
| 120 | 260 (0.12) |
| 125 | 260 (0.63) |
| 130 | 260 (7.10) |
| 140 | 260 (17.50) |
| 150 | 260 (1.93) |
| 160 | 260 (0.39) |
| 170 | — |
| 180 | 260 (0.13) |
| 190 | — |
| 200 | — |

Fractions 125–180 are combined and this solution (ADA-100A, 1300 ml) is used for the chromatography described below.

c. Amberlite XAD-2 Chromatography. Removal of THAM Acetate Buffer from ADA-100A

The column is prepared from 200 ml of Amberlite XAD-2. Prep ADA-100A is passed over the column. The spent is discarded. The column is washed with 1 L of water. The wash is discarded. The column is eluted with methanol-water (70:30 V/V). The following fractions are obtained:

| Fraction No. | Volume | UV λ max (OD) |
|---|---|---|
| 1 | 100 ml | no maximum |
| 2 | 200 ml | 260 (52.4) |
| 3 | 200 ml | 260 (12.2) |
| 4 | 500 ml | 260 (1.55) |
| 5 | 500 ml | 260 (0.16) |

Fractions 2, 3 and 4 are combined, concentrated to an aqueous solution and freeze-dried to give prep ADA-101.1, 690 mg.

Prep ADA-101.1 has biological properties, and UV, IR, C-13 and proton-NMR identical to those of pirlimycin 3-(5'-adenylate).

EXAMPLE 10

Adenylylation of Pirlimycin by Cell-Free Extracts of *Streptomyces rochei*

*Streptomyces rochei*, NRRL 3533, is grown in a medium consisting of yeast extract (Difco), 4 g/l; peptone (Difco), 4 g/l; glucose, 10 g/l; $K_2HPO_4$, 4 g/l; $KH_2PO_4$, 2 g/l; and $MgSO_4.7H_2O$, 0.5 g/l for 2 days at 28° C. on a rotary shaker. The mycelial growth obtained is used to inoculate the same medium in shaker flasks or fermentors.

The mycelia of *S. rochei* are harvested by centrifugation and washed once with water. The cell-free extract is prepared by lysozyme treatment or ultrasonic disruption of the cell walls. The lysate is centrifuged to remove unbroken cells and the supernatent is used to ribonucleotidylate pirlimycin.

The reaction mixture contains 0.2 ml sodium acetate buffer (0.1 M pH 6.0) 0.2 ml $MgCl_2$ (0.2 M), 0.2 ml ATP (0.1 M, pH 8.0), 0.4 ml pirlimycin (0.27 mm) and 1 ml of the *S. rochei* lysate. Incubation is carried out at 28° C. Samples are assayed by HPLC after 30 and 60 minutes of incubation. At 60 minutes a quantitative conversion to pirlimycin adenylate is recorded.

EXAMPLE 11

Adenylylation of Pirlimycin by Resting Cells of *Streptomyces rochei*

In a similar procedure as described in Example 10, cells of *S. rochei* are harvested and left intact. These resting cells are resuspended in potassium phosphate buffer (pH 5.0) supplemented with 0.5 gm/l $MgSO_4.7H_2O$. Pirlimycin is added at 1.5 mg/ml and incubation carried out at 31° C. on a rotary shaker for 24 hours. An HPLC assay indicates pirlimycin 3-(5'-adenylate) and pirlimycin 3-(5'-guanylate) are formed.

EXAMPLE 12

Upon substituting the cell-free extracts or resting cells of *S. rochei* in Examples 2, 3, 4, 5 and 6 for *S. coelicolor*, there is obtained the compounds obtained in said examples.

*S. rochei*, NRRL 3533, and *S. coelicolor*, NRRL 3532, are known microbes which are available to the public upon request from the NRRL repository. The address of this repository is as follows: Northern Utilization and Research Division, Agricultural Research Service, U.S. Department of Agriculture, Peoria, ILL., U.S.A. Since the compounds of the subject invention are active against various Gram-positive and Gram-negative microbes, they can be used in various environments to inhibit such microbes. For example, they can be used as disinfectants to inhibit *S. aureus* on washed and stacked food utensils contaminated with this bacterium. They also can be used as disinfectants on various dental and medical equipment contaminated with *S. aureus*. Further, the compounds of the invention can be used as bacteriostatic rinses for laundered clothes, and for impregnating papers and fabrics; and, they are also useful for suppressing the growth of sensitive organisms in plate assays and other microbiological media.

The compounds of the present invention are also useful in the treatment of diseases caused by members of the genus Mycoplasma, the most commonly known forms are PPLO (pleuropneumonia-like organisms) such as *M. hominis, M. salivarium, M. mycoides, M. hyopneumonia, M. hyorhinis, M. gallisepticum, M. arthriditis* and other species in man and animals, including domestic animals such as sheep, dogs, cattle, swine, and poultry (e.g., chickens, turkeys, ducks, and geese) and laboratory animals (e.g., rats and mice).

The U-57930 3-(5'-ribonucleotides) can be used in the treatment of kidney and other infections when L forms of gram-negative and gram-positive bacteria are present, for example, L forms of *P. mirabilis.*

Since the compounds of the subject invention are amphoteric substances, they can form salts with both acids and bases by using standard procedures. Examples of inorganic acids which can be used to form salts are hydrochloric, sulfuric, phosphoric, and the like. Examples of inorganic bases are hydroxides of sodium, potassium, calcium, lithium, and the like. Salts of the compounds can be used for the same purposes as the parent compounds.

The compounds of the subject invention are useful as antibacterial agents in suitable compositions. These compositions are preferably presented for administration to humans and animals in unit dosage forms, such as tablets, capsules, pills, powders, granules, sterile parenteral solutions or suspensions, and oral solutions or suspensions, and oil-water emulsions containing suitable quantities of the active compound in the form of the free base, or its pharmacologically acceptable salts.

For oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixture of polymeric acids with such materials as shellac, cetyl alcohol, cellulose acetate phthalate, styrene maleic acid copolymer and the like. Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the compound of the formulation with an inert pharmaceutical diluent and filling the mixture into a hard gelatin capsule of appropriate size. In another embodiment, capsules are prepared by filling hard gelatin capsules with polymeric acid coated beads containing a compound of the formulas. Soft gelatin capsules are prepared by machine encapsulation of a slurry of a compound of the formulas with an acceptable vegetable oil, light liquid petrolatum or other inert oil.

Fluid unit dosage forms for oral administration such as syrups, elixirs, and suspensions can be prepared. The water-soluble forms of a compound of the formulas can be dissolved in an aqueous vehicle together with sugar, aromatic flavoring agents and preservatives to form a syrup. An elixir is prepared by using a hydroalcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose, and the like.

Topical ointments can be prepared by dispersing the active compound in a suitable ointment base such as petrolatum, lanolin, polyethylene glycols, mixtures thereof, and the like. Advantageously, the compound is finely divided by means of a colloid mill utilizing light liquid petrolatum as a levigating agent prior to dispersing in the ointment base. Topical creams and lotions are prepared by dispersing the compound in the oil phase prior to the emulsification of the oil phase in water.

For parenteral administration, fluid unit dosage forms are prepared utilizing a compound of the formulas and a sterile vehicle, water being preferred. The compound, depending on the form and concentration used, can be either suspended or dissolved in the vehicle. In preparing solutions, a water-soluble form of a compound of the formulas can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. For sustained action, an intramuscular suspension is prepared with an insoluble form such as the trimethylsilyl ether or the pamoate salt. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfuls, tablespoonfuls, dropperfuls, ampuls, vials, segregated multiples of any of the foregoing, and other forms as herein described.

An active compound is compounded with a suitable pharmaceutical carrier in unit dosage form for convenient and effective administration. In the preferred embodiments of this invention, the dosage units contain 10, 25, 50, 100, 250, and 500 mg amounts of a compound of the formulas for systemic treatment; 5 to 65 percent w/v for parenteral treatment. The dosage of compositions containing an active compound and one or more other active ingredients is to be determined with reference to the usual dosage of each such ingredient.

The following examples are illustrative of the best mode contemplated by the inventor for carrying out his invention and are not to be construed as limiting.

The examples use the 3-(5'-ribonucleotide) of U-57,930E or U-60,970E as the active compound, but it should be understood that this is only exemplary of the other active compounds of the subject invention. U-60,970E is the 4-cis-n-butyl-L-pipecolic acid amide of 7-Cl-methylthiolincosaminide. Its preparation is shown in Example 7 of U.S. Pat. No. 4,278,789.

Reference hereinafter to U-57,930E or U-60,970E means the 3-(5'-ribonucleotide) of these compounds. The 3-ribonucleotides are those as disclosed herein.

Composition Example 1—Capsules

One thousand two-piece hard gelatin capsules for oral use, each containing 250 mg of U-57,930E or U-60,970E, are prepared from the following types and amounts of materials:

| U-57, 930E or U-60, 970E | 250 gm |
|---|---|
| Corn starch | 100 gm |
| Talc | 75 gm |
| Magnesium stearate | 25 gm |

The materials are thoroughly mixed and then encapsulated in the usual manner.

The foregoing capsules are useful for the systemic treatment of infection in adult humans by oral administration of one capsule every 6 hours.

Using the procedure above, capsules are similarly prepared containing U-57,930E or U-60,970E in 10, 25, 50, 100, and 500 mg amounts by substituting 10, 25, 50, 100 and 500 gm of U-57,930E or U-60,970E for the 250 gm used above.

Composition Example 2—Capsules

One thousand two-piece hard gelatin capsules for oral use, each containing 200 mg of U-57,930E or U-60,970E and 250 mg of tetracycline hydrochloride, are prepared from the following types and amounts of ingredients:

| U-57, 930E or U-60, 970E | 200 gm |
|---|---|
| Tetracycline hydrochloride | 250 gm |
| Talc | 75 gm |
| Magnesium stearate | 25 gm |

The ingredients are thoroughly mixed and then encapsulated in the usual manner.

The foregoing capsules are useful for the systemic treatment of infection in adult humans by the oral administration of one capsule every 6 hours.

Using the procedure above, capsules are similarly prepared containing U-57,930E or U-60,970E and each of the following antibiotics in place of tetracycline by substituting 250 gm of such other antibiotic for tetracycline: chloramphenicol, oxytetracycline, chlortetracycline, fumagillin, erythromycin, streptomycin, dihydronovobiocin and novobiocin. When a penicillin, such as potassium penicillin G, is to be used in place of tetracycline, 250,000 units per capsule is employed.

Such combination products are useful for the systemic treatment of mixed infections in adult humans by the oral administration of one capsule every 6 hours.

Composition Example 3—Tablets

One thousand tablets for oral use, each containing 500 mg of U-57,930E or U-60,970E, are prepared from the following types and amounts of materials:

| U-57,930E or U-60,970E | 500 gm |
|---|---|
| Lactose | 125 gm |
| Corn starch | 65 gm |
| Magnesium stearate | 25 gm |
| Light liquid petrolatum | 3 gm |

The ingredients are thoroughly mixed and slugged. The slugs are broken down by forcing through a number 16 screen. The resulting granules are then compressed into tablets, each tablet containing 500 mg of U-57,930E or U-60,970E.

The foregoing tablets are useful for systemic treatment of infections in adult humans by oral administration of one tablet three times a day.

Using the above procedure, except for reducing the amount of U-57,930E or U-60,970E to 250 gm, tablets containing 250 mg of U-57,930E or U-60,970E are prepared.

Composition Example 4—Tablets

One thousand oral tablets, each containing 250 mg of U-57,930E or U-60,970E and total of 250 mg (83.3 mg each) of sulfadiazine, sulfamerazine, and sulfamethazine, are prepared from the following types and amounts of materials:

| U-57,930E or U-60,970E | 250 gm |
|---|---|
| Sulfadiazine | 83.3 gm |
| Sulfamerazine | 83.3 gm |
| Sulfamethazine | 83.3 gm |
| Lactose | 50 gm |
| Corn starch | 50 gm |
| Calcium stearate | 25 gm |
| Light liquid petrolatum | 5 gm |

The ingredients are thoroughly mixed and slugged. The slugs are broken down by forcing through a number sixteen screen. The resulting granules are then compressed into tablets, each containing 250 mg of U-57,930E or U-60,970E and a total of 250 mg (83.3 mg each) of sulfadiazine, sulfamerazine, and sulfamethazine.

The foregoing tablets are useful for systemic treatment of infections by the oral administration of four tablets first and then one every six hours.

For the treatment of urinary infections, the triple sulfas in the above formulation is advantageously replaced by 250 gm of sulfamethylthiadiazole or 250 gm of sulfacetamide.

Composition Example 5—Oral Syrup

One thousand cc of an aqueous suspension for oral use, containing in each 5 cc dose 250 mg of U-57,930E or U-60,970E and 500 mg of total sulfas is prepared from the following types and amounts of ingredients:

| U-57, 930E or U-60, 970E | 50 gm |
|---|---|
| Sulfadiazine | 33.3 gm |
| Sulfamerazine | 33.3 gm |
| Sulfamethazine | 33.3 gm |
| Citric acid | 2 gm |
| Benzoic acid | 1 gm |
| Sucrose | 700 gm |
| Tragacanth | 5 gm |
| Lemon oil | 2 cc |
| Deionized water, q.s. | 1000 cc |

The citric aid, benzoic acid, sucrose, tragacanth, and lemon oil are dispersed in sufficient water to make 850 cc of solution. The U-57,930E or U60,970E and finely divided sulfas are stirred into the syrup until uniformly distributed. Sufficient water is added to make 1000 cc.

The composition so prepared is useful in the systemic treatment of pneumonia in adult humans at a dose of 1 tablespoonful (10 cc) 4 times a day.

Composition Example 6—Parenteral Solution

A sterile aqueous solution for intramuscular use, containing 200 mg of U-57,930E or U-60,970E in 1 cc is prepared from the following types and amounts of materials:

| U-57, 930E or U-60, 970E | 200 gm |
|---|---|
| Lidocaine hydrochloride | 4 gm |
| Methylparaben | 2.5 gm |
| Propylparaben | 0.17 gm |
| Water for injection, q.s. | 1,000 cc |

The ingredients are dissolved in the water and the solution sterilized by filtration. The sterile solution is filled into vials and the vials sealed.

Composition Example 7—Parenteral Preparation

A sterile aqueous composition for intramuscular use, containing in 1 cc 200 mg of U-57,930E or U-60,970E and 400 mg of spectinomycin sulfate is prepared from the following types and amounts of ingredients:

| U-57,930E or U-60,970E | 200 gm |
|---|---|
| Spectinomycin sulfate | 400 gm |
| Lactose | 50 gm |
| Water for injection, q.s. | 1,000 cc |

The U-57,930E or U-60,970E, spectinomycin sulfate, and lactose are dispersed in the water and sterilized. The sterile composition, in the amount of 2 cc, is filled aseptically into sterile vials.

Composition Example 8—Topical Ointment

One thousand gm of 0.25% ointment is prepared from the following types and amounts of ingredients:

| U-57,930E or U-60,970E | 2.5 gm |
|---|---|
| Zinc oxide | 50 gm |
| Calamine | 50 gm |
| Liquid petrolatum (heavy) | 250 gm |
| Wool fat | 200 gm |
| White petrolatum, q.s. | 1,000 gm |

The white petrolatum and wool fat are melted and 100 gm of liquid petrolatum added thereto. The U-57,930E or U-60,970E, zinc oxide and calamine are added to the remaining liquid petrolatum and the mixture milled until the powders are finely divided and uniformly dispersed. The powder mixture is stirred into the white petrolatum mixture and stirring continued until the ointment congeals.

The foregoing ointment is usefully applied topically to the skin of mammals for the treatment of infection.

The foregoing composition can be prepared by omitting the zinc oxide and calamine.

Following the procedure above, ointments are similarly prepared containing U-57,930E or U-60,970E in 0.5, 1, 2, and 5% amounts by substituting 5, 10, 20 and 50 gm of U-57,930E or U-60,970E for the 2.5 gm used above.

Composition Example 9—Cream

One thousand gm of a vaginal cream are prepared from the following types and amounts of ingredients:

| U-57,930E or U-60,970E | 50 gm |
|---|---|
| Tegacid Regular[1] | 150 gm |
| Spermaceti | 100 gm |
| Propylene glycol | 50 gm |
| Polysorbate 80 | 5 gm |
| Methylparaben | 1 gm |
| Deionized water, q.s. | 1,000 gm |

[1]Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm of water and the propylene glycol, Polysorbate 80, and U-57,930E or U-60,970E are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by incorporating 2.5 gm of citric acid and 0.2 g of dibasic sodium phosphate dissolved in about 50 gm of water. Finally, sufficient water is added to bring the final weight to 1,000 gm and the preparation stirred to maintain homogeneity until cooled and congealed.

The foregoing composition is useful for the treatment of vaginal infections in humans.

Composition Example 10—Ointment, Ophthalmic

One thousand gm of an ophthalmic ointment containing 0.5% U-57,930E or U-60,970E are prepared from the following types and amounts of ingredients:

| U-57,930E or U-60,970E | 5 gm |
|---|---|
| Bacitracin | 12.2 gm |
| Polymyxin B sulfate (10,000 units/mg) | 1 gm |
| Light liquid petrolatum | 250 gm |
| Wool fat | 200 gm |
| White petrolatum, q.s. | 1,000 gm |

The solid ingredients are finely divided by means of an air micronizer and added to the light liquid petrolatum. The mixture is passed through a colloid mill to uniformly distribute the micronized particles. The wool fat and white petrolatum are melted together, strained, and the temperature adjusted to 45°–50° C. The liquid petrolatum slurry is added and the ointment stirred until congealed. Suitably the ointment is packaged in one dram ophthalmic tubes.

The foregoing ointment is usefully applied to the eye for treatment of localized infection in humans and other animals.

Advantageously the foregoing composition can contain 5 gm (0.5%) of methylprednisolone for the treatment of inflammation, and, alternatively, the bacitracin and polymyxin B sulfate can be omitted.

Composition Example 11—Eye-Ear Drops

One thousand cc of a sterile aqueous solution for eye or ear use containing 10 mg of U-57,930E or U-60,970E and 5 mg of methylprednisolone in each cc is prepared from the following types and amounts of ingredients:

| | |
|---|---|
| U-57,930E or U-60,970E | 10 gm |
| Methylprednisolone phosphate sodium | 5 gm |
| Sodium citrate | 4.5 gm |
| Sodium bisulfite | 1 gm |
| Polyethylene glycol 4000 | 120 gm |
| Myristyl-γ-picolinium chloride | 0.2 gm |
| Polyvinylpyrrolidone | 1 gm |
| Deionized water, q.s. ad | 1000 cc |

The ingredients are dissolved in the water and the resulting solution is sterilized by filtration. The solution is aseptically filled into sterile dropper containers.

The composition so prepared is useful in the topical treatment of inflammation and infection of the eye and ear as well as other sensitive tissues of the animal body.

Composition Example 12—Troches

Ten thousand troches are prepared from the following types and amounts of ingredients:

| | |
|---|---|
| U-57,930E or U-60,970E | 100 gm |
| Neomycin sulfate | 50 gm |
| Polymyxin B sulfate (10,000 units/mg) | 1 gm |
| Ethyl aminobenzoate | 50 gm |
| Calcium stearate | 150 gm |
| Powdered sucrose, q.s. | 5,000 gm |

The powdered materials are mixed thoroughly and then compressed into half gram troches following the usual techniques for the preparation of compressed tablets.

The troches are held in the mouth and allowed to dissolve slowly to provide treatment for the mouth and throat of humans.

Composition Example 13—Suppository, Rectal

One thousand suppositories, each weighing 2.5 gm and containing 100 mg of U-57,930E or U-60,970E are prepared from the following types and amounts of ingredients:

| | |
|---|---|
| U-57, 930E or U-60, 970E | 100 gm |
| Polymyxin B sulfate (10,000 units/mg) | 1.25 gm |
| Methylprednisolone | 1 gm |
| Ethyl aminobenzoate | 75 gm |
| Zinc oxide | 62.5 gm |
| Propylene glycol | 162.5 gm |
| Polyethylene glycol 4,000 q.s. | 2,500 gm |

The U-57,930E or U-60,970E, polymyxin B sulfate, methylprednisolone, ethyl aminobenzoate, and zinc oxide are added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C.

The composition is allowed to cool and solidify and then removed from the mold and each suppository foil wrapped.

The foregoing suppositories are inserted rectally for local treatment of inflammation and infection.

Alternatively, the foregoing composition can be prepared omitting the steroid.

Composition Example 14—Mastitis Ointment

One thousand gm of an ointment for the treatment of mastitis in dairy cattle is prepared from the following types and amounts of ingredients:

| | |
|---|---|
| U-57, 930E or U-60, 970E | 25 gm |
| Methylprednisolone acetate | 0.5 gm |
| Light liquid petrolatum | 300 gm |
| Chlorobutanol, anhydrous | 5 gm |
| Polysorbate 80 | 5 gm |
| 2% Aluminum monostearate-peanut oil gel | 400 gm |
| White petrolatum, q.s. | 1000 gm |

The U-57,930E or U-60,970E and methylprednisolone acetate are milled with the light liquid petrolatum until finely divided and uniformly dispersed. The chlorobutanol, polysorbate 80, peanut oil gel and white petrolatum are heated to 120° F. to form a melt and the liquid petrolatum dispersion stirred in. With continued stirring, the dispersion is allowed to cool (and congeal) to room temperature and is filled into disposable mastitis syringes in 10 gm doses.

Composition Example 15—Animal Feed

One thousand gm of a feed mix is prepared from the following types and amounts of ingredients:

| | |
|---|---|
| U-57, 930E or U-60, 970E | 10 gm |
| Soybean meal | 400 gm |
| Fish meal | 400 gm |
| Wheat germ oil | 50 gm |
| Sorghum molasses | 140 gm |

The ingredients are mixed together and pressed into pellets. The composition can be fed to laboratory animals, i.e., rats, mice, guinea pigs, and hamsters for prophylaxis during shipping.

For other animals such as poultry, e.g., chickens, ducks, turkeys, and geese, the composition can be added to the animal's regular feed in an amount calculated to give the desired dose of U-57,930E or U-60,970E.

Composition Example 16

Following the procedure of each of the preceding Composition Examples 1-15, inclusive, each antibacterially-active compound of the subject invention is substituted in an equivalent amount for the U-57,930E or U-60,970E shown in the example to provide therapeutic properties.

Similarly, each of the above free base compounds can be used in the form of a pharmaceutically (or pharmacologically) acceptable salt, e.g., hydrochloride, sulfate, phosphoric, sodium, potassium, calcium, and lithium.

CHART 1

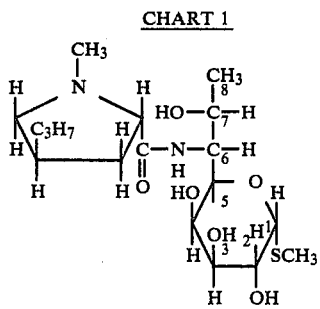
(1)

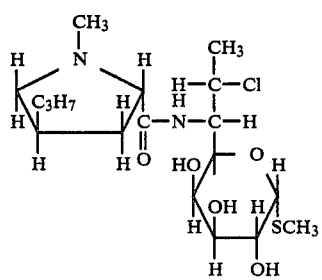
(2)

CHART 2

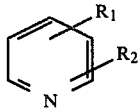

wherein R$_1$, which can be singly or multiply substituted in any position of the pyridine ring not already substituted by R$_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and isomeric forms thereof, wherein n is an integer of from 1 to 8, inclusive, R$_4$ and R$_5$ are H or alkyl of from 1 to 8 carbon atoms, inclusive, and isomeric forms thereof; wherein R$_2$, which can be singly substituted in any position of the pyridine ring not already substituted by R$_1$, is

and X is the amino function of a compound selected from the group 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxymethyl 1-thio-α-lincosaminide, 7-deoxy-7(S)-(methylthio)-methyl 1-thio-α-lincosaminide, 7-deoxy-7(S)-(2-hydroxyethylthio)-methyl 1-thio-α-linconsaminide and 7-deoxy-7(S)-(3-hydroxypropylthio)-methyl 1-thio-α-lincosaminide; and the pharmaceutically acceptable salts thereof.

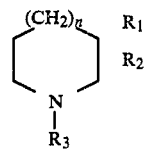

wherein R$_1$ and R$_2$, which can be in the 2, 3, 4, 5, 6, 7, 8, or 9 position of the ring, are as defined above; wherein R$_3$ is selected from the group consisting of H, CH$_3$, C$_2$H$_5$, and —CH$_2$—CH$_2$—OH; wherein n is an integer of from 1 to 4, inclusive; and the pharmaceutically acceptable salts thereof.

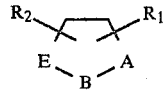

wherein A, B and E are selected from the group consisting of nitrogen, oxygen, sulfur and CR$_1$R$_1$; R$_1$ and R$_2$ are as defined above, and can be attached to any ring carbon or nitrogen atom; R$_1$ can be multiply attached to any ring carbon atom, and the pharmaceutically acceptable salts thereof.

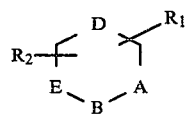

wherein A, B, D and E are selected from the group consisting of nitrogen, oxygen, sulfur and CR$_1$R$_1$; R$_1$ and R$_2$ are as defined above and can be attached to any ring carbon or nitrogen atom; R$_1$ can be multiply attached to any ring carbon atom, and the pharmaceutically acceptable salts thereof.

CHART 3

The ribonucleotide part of the 3-(5'-ribonucleotides) of lincosaminides can be represented by the following formula:

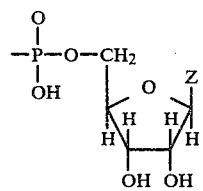

wherein Z can be:
(1) purines of the general formula

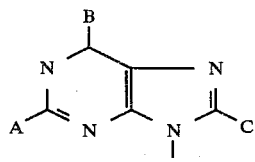

(2) pyrimidines of the general formulae

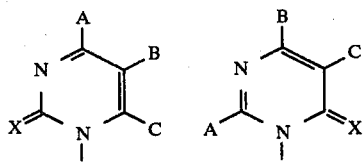

wherein A, B, and C can be alkyl (C$_1$–C$_8$); OH; NH$_2$; —SH; OR; NHR; NR$_1$R$_2$; SR; wherein R, R$_1$ and R$_2$ are alkyl (C$_1$–C$_8$); CN, COOH and NO$_2$; wherein X is O, S or NH.

CHART 4

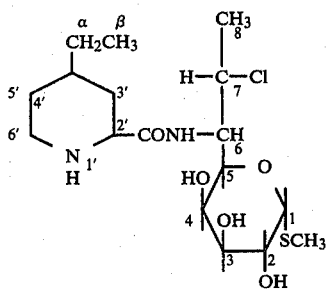

Pirlimycin

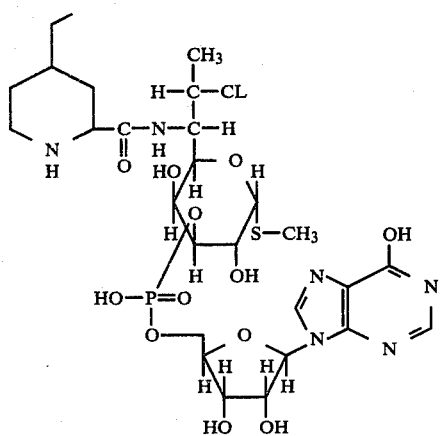

Pirlimycin 3-(5'-inosinate)

We claim:
1. A process for preparing 3-(5'-ribonucleotides) of a compound of the formula

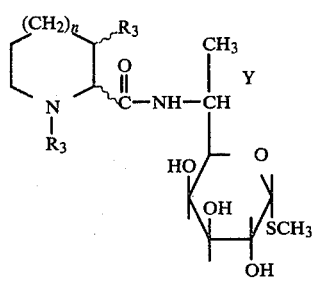

wherein R$_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and branched chain isomers thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and branched chain isomers thereof, wherein n is an integer of from 1 to 8, inclusive, R$_4$ and R$_5$ are H or alkyl of from 1 to 8 carbon atoms, inclusive, and branched chain isomers thereof; wherien R$_3$ is selected from the group consisting of H, CH$_3$, C$_2$H$_5$, and —CH$_2$—CH$_2$—OH; wherein n is an integer of from 1 to 4, inclusive, wherein Y is selected from the group consisting of 7(S)-halo and 7(R)-halo; and the pharmaceutically acceptable salts thereof which comprises contacting resting cell or cell-free extracts of *Streptomyces rochei*, NRRL 3533, with a compound of the above formula, and recovering the desired 3-(5'-ribonucleotide) from the reaction mixture.

2. A process for preparing the 3-(5'-ribonucleotides) of a compound of the formula

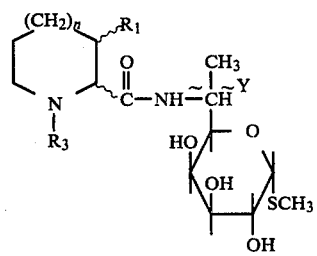

wherein R$_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and branched chain isomers thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and branched chain isomers thereof, wherein n is an integer of from 1 to 8, inclusive, R$_4$ and R$_5$ are H or alkyl of from 1 to 8 carbon atoms, inclusive, and branched chain isomers thereof; wherien R$_3$ is selected from the group consisting of H, CH$_3$, C$_2$H$_5$, and —CH$_2$—CH$_2$—OH; wherein n is an integer of from 1 to 4, inclusive, wherein Y is selected from the group consisting of 7(S)-halo and 7(R)-halo; and the pharmaceutically acceptable salts thereof which comprises contacting a cell-free extract of *Streptomyces coelicolor* NRRL 3532, with a compound of the above formula, and recovering the desired 3-(5'-ribonucleotide) from the reaction mixture.

3. Pirlimycin 3-(5'-inosinate) having the formula

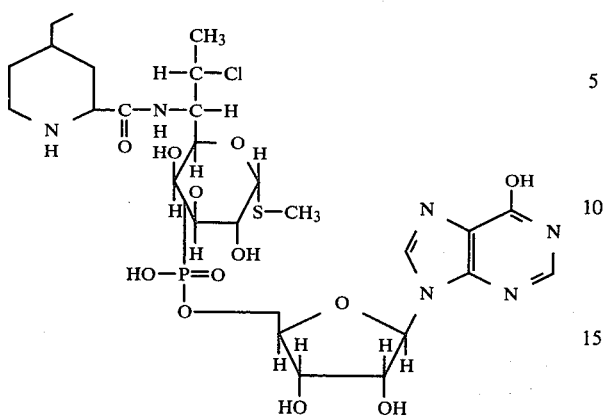

4. A process for preparing 3-(5'-ribonucleotides) of a compound of the of the formula

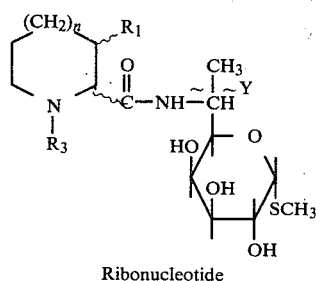
Ribonucleotide wherein $R_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and branched chain isomers thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and branched chain isomers thereof, wherein n is an integer of from 1 to 8, inclusive, RHD 4 and $R_5$ are H or alkyl of from 1 to 8 carbon atoms, inclusive, and branched chain isomers thereof; wherein $R_3$ is selected from the group consisting of H, $CH_3$, $C_2H_5$, and $-CH_2-CH_2-OH$; wherein n is an integer of from 1 to 4, inclusive, wherein Y is selected from the group consisting of 7(S)-halo and 7(R)-halo; and the pharmaceutically acceptable salts thereof; wherein the ribonucleotide can be represented by the following formula:

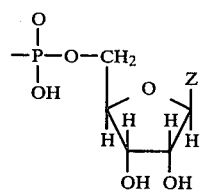

wherein Z can be:
(1) purines of the general formula

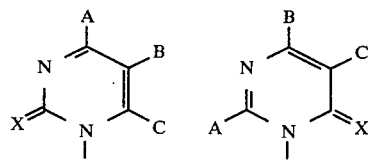

(2) pyrimidines of the general formulae

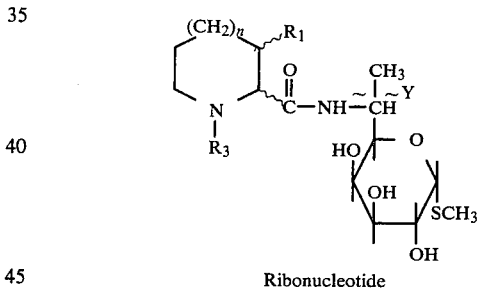

wherein A, B, and C can be alkyl $(C_1-C_8)$; OH, $NH_2$; $-SH$; OR; NHR; $NR_1R_2$; SR; wherein R, $R_1$ and $R_2$ are alkyl $(C_1-C_8)$; CN, COOH and $NO_2$; wherein X is O,S or NH; which comprises contacting resting cell or cell-free extracts of *Streptomyces rochei*, NRRL 3533, with a compound of the above formula, and recovering the desired 3-(5'-ribonucleotide) from the reaction mixture.

5. A process for preparing 3-(5'-ribonucleotides) of a compound of the formula

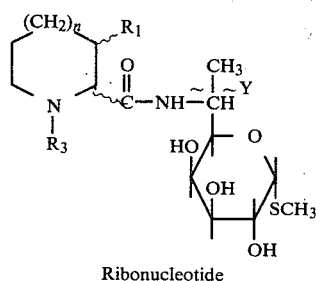
Ribonucleotide wherein $R_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and branched chain isomers thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and branched chain isomers thereof, wherein n is an integer of from 1 to 8, inclusive, $R_4$ and $R_5$ are H or alkyl of from 1 to 8 carbon atoms, inclusive, and branched chain isomers thereof; wherein $R_3$ is selected from the group consising of H, $CH_3$, $C_2H_5$, and $-CH_2-CH_2-OH$; wherein n is an integer of from 1 to 4, inclusive, wherein Y is selected from the group consisting of 7(S)-halo and 7(R)-halo; and the pharmaceutically acceptable salts thereof; wherein the ribonucleotide can be represented by the following formula:

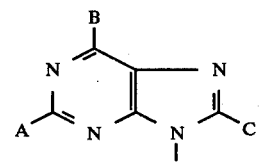

wherein Z can be:

(1) purines of the general formula

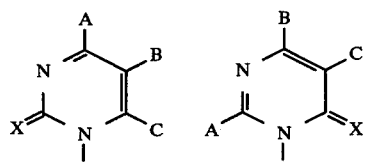

(2) pyrimidines of the general formulae wherein A, B, and C can be alkyl ($C_1$–$C_8$); OH; $NH_2$; —SH; OR; NHR; $NR_1R_2$; SR; wherein R, $R_1$ and $R_2$ are alkyl ($C_1$–$C_8$); CN, COOH and $NO_2$; wherein X is O,S or NH, which comprises contacting a cell-free extract of *Streptomyces coelicolor* NRRL 3532 with a compound of the above formula, and recovering the desired 3-(5′-ribonucleotide) from the reaction mixture.

* * * * *